United States Patent [19]

Müller et al.

[11] 4,436,814

[45] Mar. 13, 1984

[54] METHOD FOR THE RECOVERY OF ENZYMES AFTER THE TREATMENT OF STARCH-CONTAINING RAW MATERIALS USED FOR THE PRODUCTION OF FERMENTATION ALCOHOL

[75] Inventors: Hans Müller, Erlenbach; Hans-Peter Knöpfel; Felix Müller, both of Stäfa, all of Switzerland; Rolf H. Kretz, Singen, Fed. Rep. of Germany

[73] Assignee: PEC Process Engineering Company, Männedorf, Switzerland

[21] Appl. No.: 325,819

[22] Filed: Nov. 30, 1981

[30] Foreign Application Priority Data

Dec. 2, 1980 [CH] Switzerland ............... 8893/80

[51] Int. Cl.$^3$ ............... C12P 19/20; C12P 19/14; C12P 7/14; C12N 9/28
[52] U.S. Cl. ............... 435/162; 435/96; 435/99; 435/813; 435/202; 435/205
[58] Field of Search ............... 435/93, 96, 99, 161, 435/162, 202, 205

[56] References Cited

U.S. PATENT DOCUMENTS 3,236,740 2/1966 Smith et al. ............... 435/161
4,287,304 9/1981 Muller et al. ............... 435/162
4,316,956 2/1982 Lutzen ............... 435/96

*Primary Examiner*—Lionel M. Shapiro
*Attorney, Agent, or Firm*—Michael J. Striker

[57] ABSTRACT

In a method for the recovery of enzymes, the activity of which after the treatment of starch-containing raw materials used for the production of fermentation alcohol is still not exhausted, the liquid phase containing solutions with still active enzymes after the first separation of the protein fraction is led to a fermentation, then a distillation. The wash water for the protein fraction is provided with a portion of the total amount of alpha-amylase necessary for starch hydrolysis of the raw material and then solids are again separated. The enzyme-containing wash water for the second separated solids is led back into the first enzymatic degradation stage simultaneously with a portion of the slop coming from the distillation.

4 Claims, 1 Drawing Figure

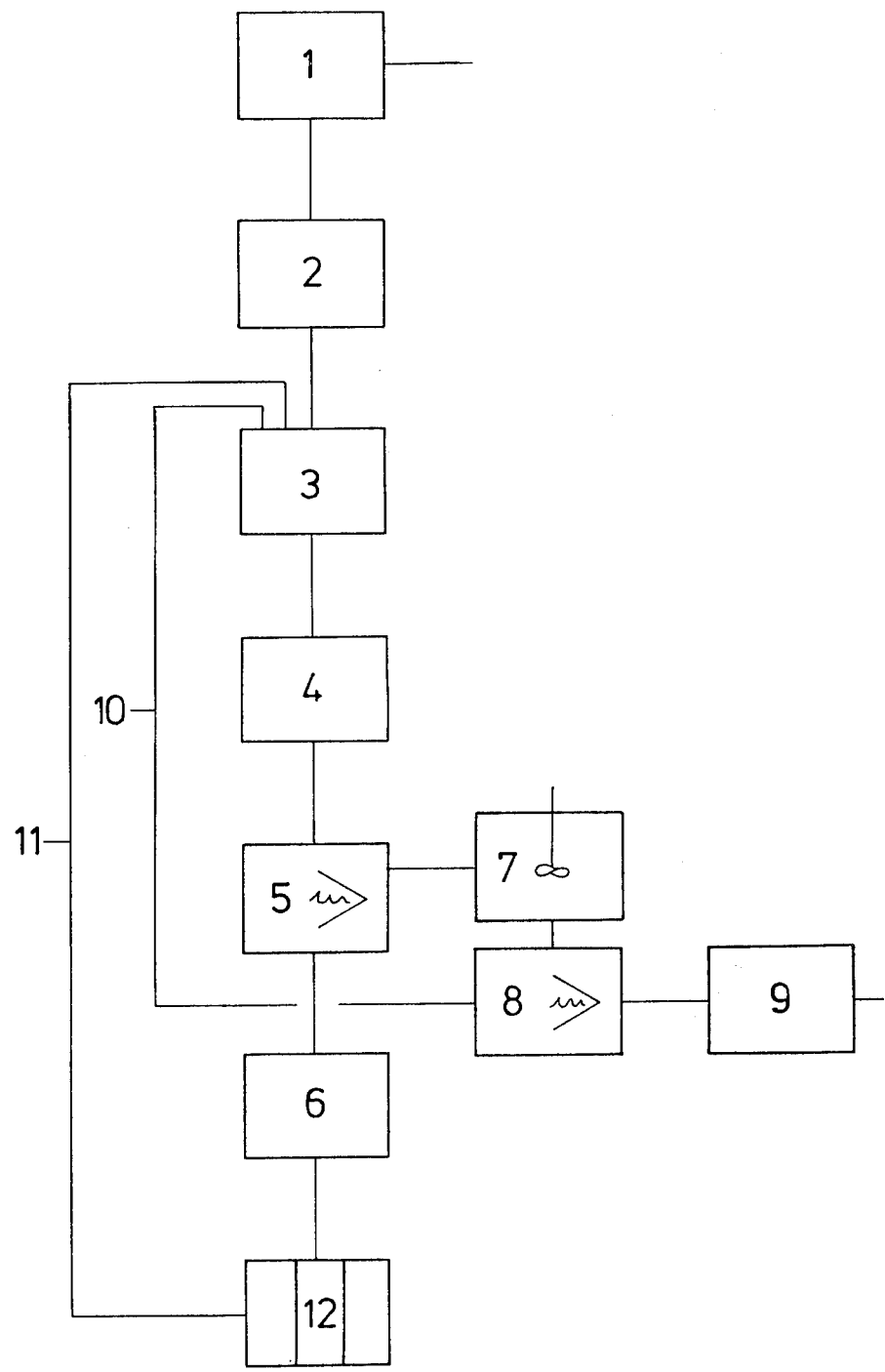

METHOD FOR THE RECOVERY OF ENZYMES AFTER THE TREATMENT OF STARCH-CONTAINING RAW MATERIALS USED FOR THE PRODUCTION OF FERMENTATION ALCOHOL

BACKGROUND OF THE INVENTION

This invention concerns a method for the utilization of active amylolytic enzymes after the treatment of starch-containing raw materials used for the production of fermentation alcohol.

Grain and other starch-containing raw materials are used for the production of fermentation alcohol. With the use of grain, initially a so-called mash is prepared, in known manner, through the mash process. The mash process cam be considerably shortened through the addition of amylolytic enzymes such as alpha-amylase, beta-glucosidase, beta-amylase, among others (for example pullulanase), in a two-stage enzymatic degradation process. Since the degradation of the starch into fermentable sugars should take place as extensively as possible, on economical grounds, it must be worked up with an excess of enzymes. In order to obtain a clear fermentable wort, the protein contained in the grain is separated with other solids, and used as fodder. The wash water for the separated protein fraction is recycled.

Not only in the wash water for the separated solids, but also in the fermented wort, which is obtained through distillation after the separation of alcohol, as so-called distiller's wash or slop, still active amylolytic enzymes are contained, in particular temperature-stable alpha-amylase.

SUMMARY OF THE INVENTION

It is therefore an object of the present invention to provide a method which makes possible the use of these still active amylolytic enzymes.

This object is attained according to the present invention through a method for the use of active amylolytic enzymes after the treatment of starch-containing raw materials used for the production of fermentation alcohol, which is thereby characterized in that the still active enzyme-containing solutions are led back into the first enzyme degradation stage, after separation of the protein fraction.

After the treatment of the starch there follows a first separation of solids, the greatest portion of which is composed of protein, cellulose-containing fiber material and untreated starch. The wash water for these first separated solids is, in advantageous manner, provided with alpha-amylase, and the so-obtained protein cake is suspended therein. The portion of alpha-amylase provided at this point in the process can amount up to half of the amount necessary for the starch-treatment of the raw grain. The addition of the enzyme at this stage in the process has the advantage that a further portion of the untreated starch, remaining with the albumen, becomes liquefied and eliminated. After a second separation of the so-refined protein, the wash water for the thus obtained second protein fraction is led back into the first enzymatic degradation stage.

At the same time, a portion of the slop coming from the distillation of the fermented mash, which can also contain still active enzymes, can likewise be added to this first enzymatic degradation stage.

The novel features which are considered characteristic for the present invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE, in the form of a flow chart, illustrates the method according to the present invention.

DESCRIPTION OF THE PREFERRED EMBODIMENTS

In a mill 1, grain kernels are ground and then led into container 2, where they are stirred to a paste and diluted. In a container 3 there follows a first enzymatic treatment with alpha-amylase solution, whereby according to the present invention only about half of the amount of this enzyme necessary for starch degradation is needed. The treatment follows for about 2 hours at a temperature between 80 and 90° C. In a second enzyme stage, in container 4, after cooling, the product from container 3 is saccharified with amyloglucosidase. The separation of solids follows by means of decanter 5, whereby the liquid phase is led into fermentation 6 for the production of ethanol. The residue following separation of the liquid phase is suspended with water in container 7, with the addition and suspension of about half of the amount of alpha-amylase necessary for starch hydrolysis of the raw material. The enzyme-containing liquid is separated from solids across a super-decanter 8, and the protein is collected in a container 9 for further working up. The dried filter cake displays a protein content of about 60% by weight. The liquid, i.e. the enzyme-containing wash water, is led back across conduit 10 into container 3 of the first enzyme stage.

The advantage of the alpha-amylase treatment before the last washing of the protein cake is that the so-obtained dried filter cake displays a protein content up to 60%. Such a high protein content is not obtainable with the known methods.

The fermented mash from fermenter 6 is led into distillation apparatus 12 for the production of ethanol. The alpha-amylase, which has good temperature stability, and which stems from the excess in the first enzyme stage, always still displays a certain activity in the slop obtained from distillation 12. A portion, up to 30%, of the obtained slop is therefore likewise led across a conduit 11 into the first enzymatic degradation in container 3, and thereby contributes, according to its activity, to the starch hydrolysis.

The main advantage of the method according to the present invention is thus in a saving of alpha-amylase. The production of fermentation alcohol can thereby be accomplished more economically.

It will be understood that each of the elements described above, or two or more together, may also find a useful application in other types of enzymatic treatments differing from the types described above.

While the invention has been illustrated and described as embodied in a method for the recovery of enzymes after the treatment of starch-containing raw materials used for the production of fermentation alcohol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In the method of treating starch-containing raw materials for the production of fermentation alcohol, by, in order, the steps of enzymatically degrading said starch-containing raw materials, separating solids from said raw materials, thereby, providing a liquid phase and a first solids phase in the form of a filter cake, subjecting said liquid phase to a fermentation for the production of ethanol, suspending said solids phase in water, separating solids from said solids phase suspended in water, thereby providing an enzyme-containing wash water phase and a second solids phase, and collecting said second solids phase for further working-up, the improvement comprising leading said enzyme-containing wash water back into said step of enzymatically degrading.

2. Method according to claim 1, further comprising adding alpha-amylase to said water after the first separation of solids before said suspending said solids phase.

3. Method according to claim 2, wherein about half of the total amount of alpha-amylase necessary for starch hydrolysis of the raw material is added to said water.

4. Method according to claim 1, wherein said second solids phase displays a protein content of about 60% by weight.

* * * * *